(12) United States Patent
Kashiwa

(10) Patent No.: US 12,370,094 B2
(45) Date of Patent: Jul. 29, 2025

(54) CONNECTING-TYPE DISPOSABLE WEARING ARTICLE

(71) Applicant: DAIO PAPER CORPORATION, Ehime (JP)

(72) Inventor: Masaaki Kashiwa, Tochigi (JP)

(73) Assignee: Daio Paper Corporation, Ehime (JP)

( * ) Notice: Subject to any disclaimer, the term of this patent is extended or adjusted under 35 U.S.C. 154(b) by 430 days.

(21) Appl. No.: 17/802,049

(22) PCT Filed: Mar. 12, 2021

(86) PCT No.: PCT/JP2021/010129
§ 371 (c)(1),
(2) Date: Aug. 24, 2022

(87) PCT Pub. No.: WO2021/193151
PCT Pub. Date: Sep. 30, 2021

(65) Prior Publication Data
US 2023/0126828 A1    Apr. 27, 2023

(30) Foreign Application Priority Data
Mar. 26, 2020 (JP) .................................. 2020-056600

(51) Int. Cl.
A61F 13/15     (2006.01)
A61F 13/49     (2006.01)
A61F 13/494    (2006.01)

(52) U.S. Cl.
CPC .... *A61F 13/4942* (2013.01); *A61F 13/49017* (2013.01); *A61F 13/49058* (2013.01); *A61F 2013/4948* (2013.01)

(58) Field of Classification Search
CPC ............ A61F 13/4942; A61F 13/49017; A61F 13/49058; A61F 2013/4948
See application file for complete search history.

(56) References Cited

U.S. PATENT DOCUMENTS 5,993,433 A * 11/1999 St. Louis ............ A61F 13/4942
                                                      604/385.27
2018/0055698 A1   3/2018 Bishop et al.

FOREIGN PATENT DOCUMENTS

JP    2001-293031    10/2001
JP    2010-022587     2/2010
(Continued)

OTHER PUBLICATIONS

International Search Report for PCT/JP2021/010129, dated Jun. 1, 2021.

*Primary Examiner* — Jacqueline F Stephens
(74) *Attorney, Agent, or Firm* — Andrus Intellectual Property Law, LLP

(57) ABSTRACT

A connecting-type disposable wearing article including a three-dimensional waist gather rising from a front surface and being provided along a second blocking position disposed between first back fallen portions of a three-dimensional side gather. The three-dimensional waist gather has: a waist root portion attached along the second blocking position; a second portion extending from the waist root portion toward a waist edge side; second fallen portions formed by fixing both end portions in a width direction of the second portion in a fallen state, respectively; a second rising portion formed to be non-fixed between the second fallen portions in the second portion; and a second three-dimensional elastic member attached at least to a tip portion of the second rising portion, and at least the tip portion of the second rising portion is contracted in the width direction together with the second three-dimensional elastic member and extensible in the width direction.

5 Claims, 10 Drawing Sheets

(56) References Cited

FOREIGN PATENT DOCUMENTS

| | | |
|---|---|---|
| JP | 2016-032591 | 3/2016 |
| JP | 3-218752 | 11/2018 |
| WO | 2016/051938 | 4/2016 |
| WO | 2020/004499 | 1/2020 |

* cited by examiner

[FIG.1]
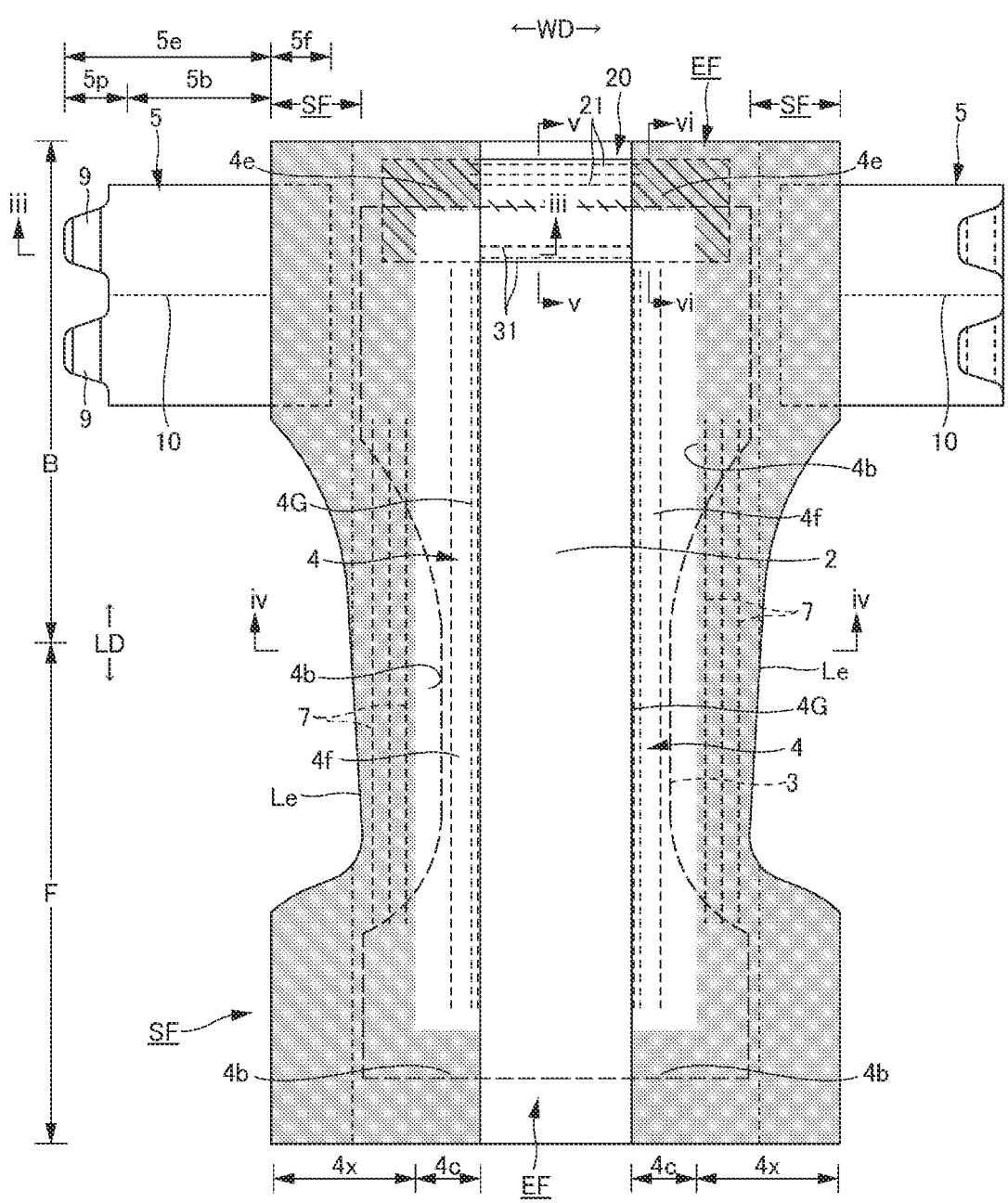

[FIG.2]
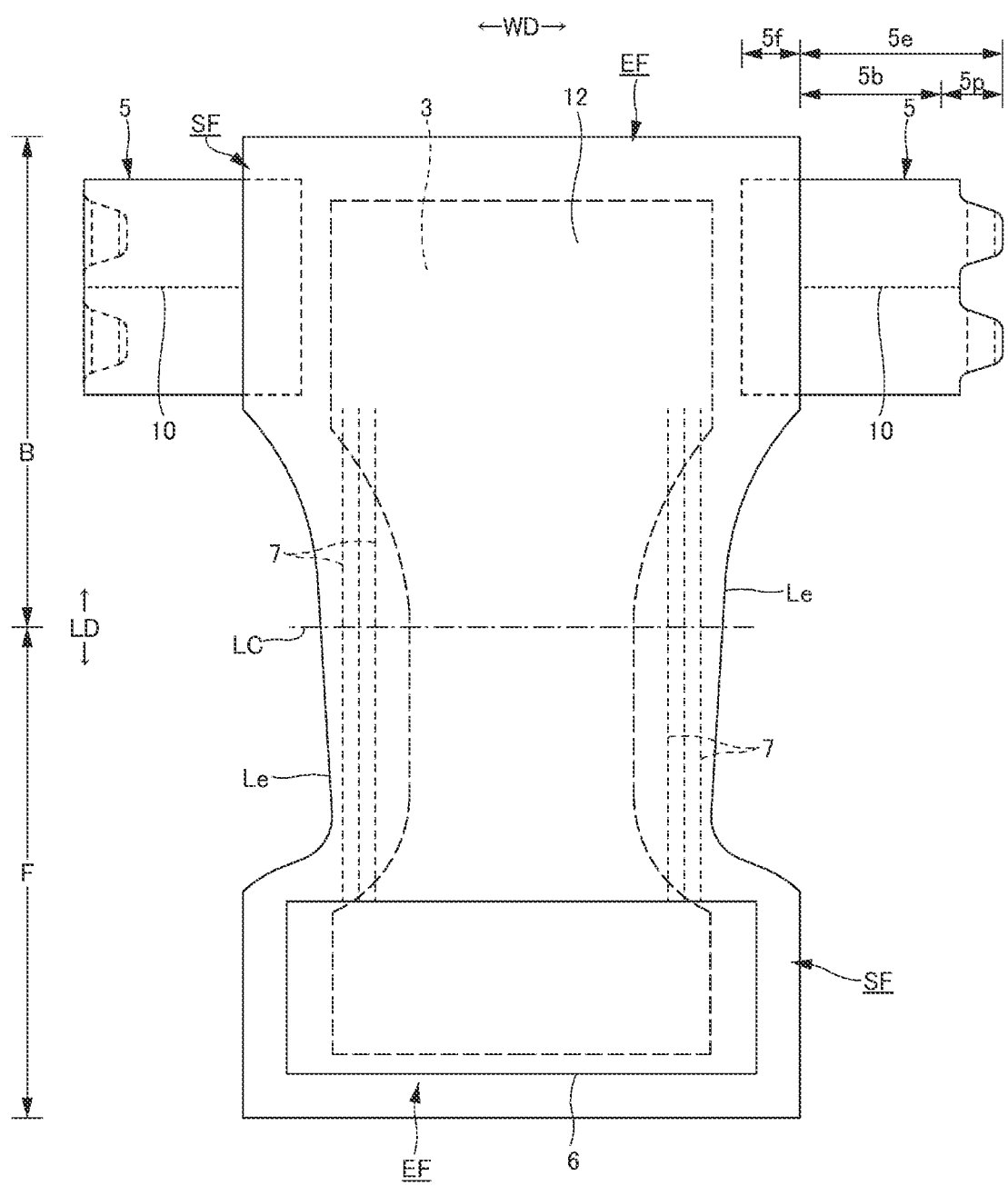

[FIG.3]
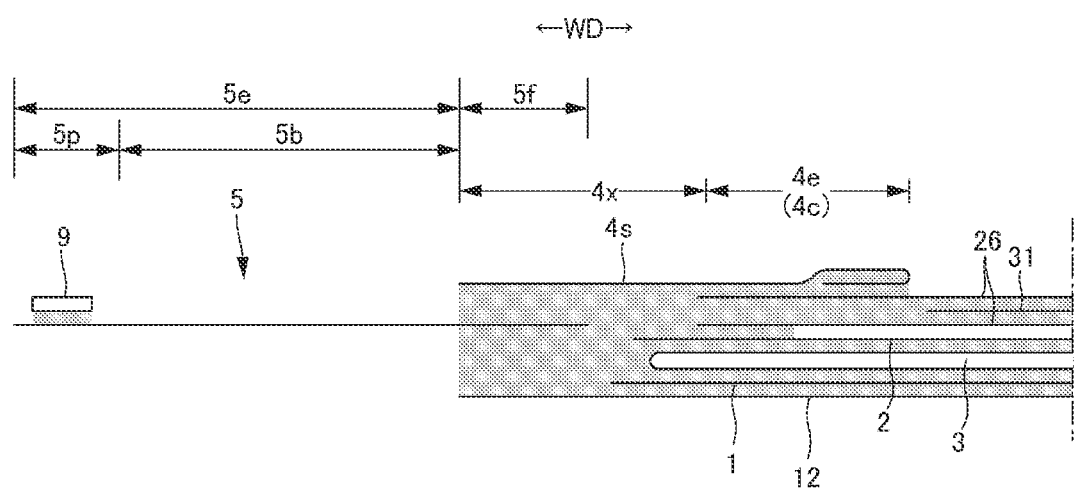

[FIG.4]
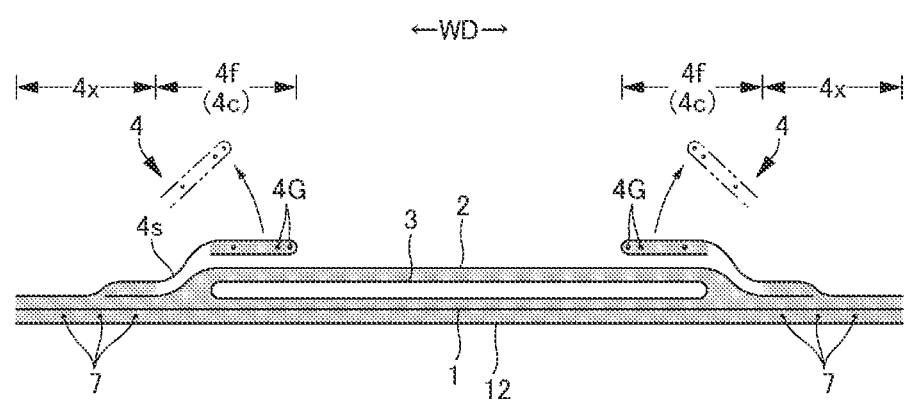

[FIG.5]
(a)
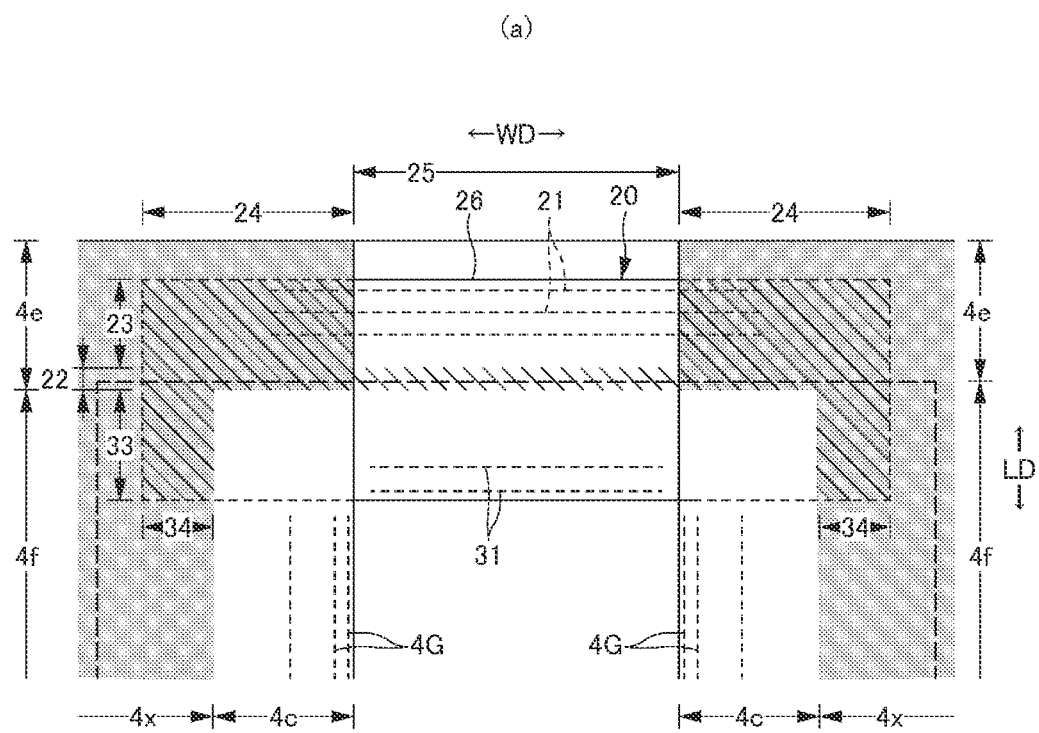
(b)
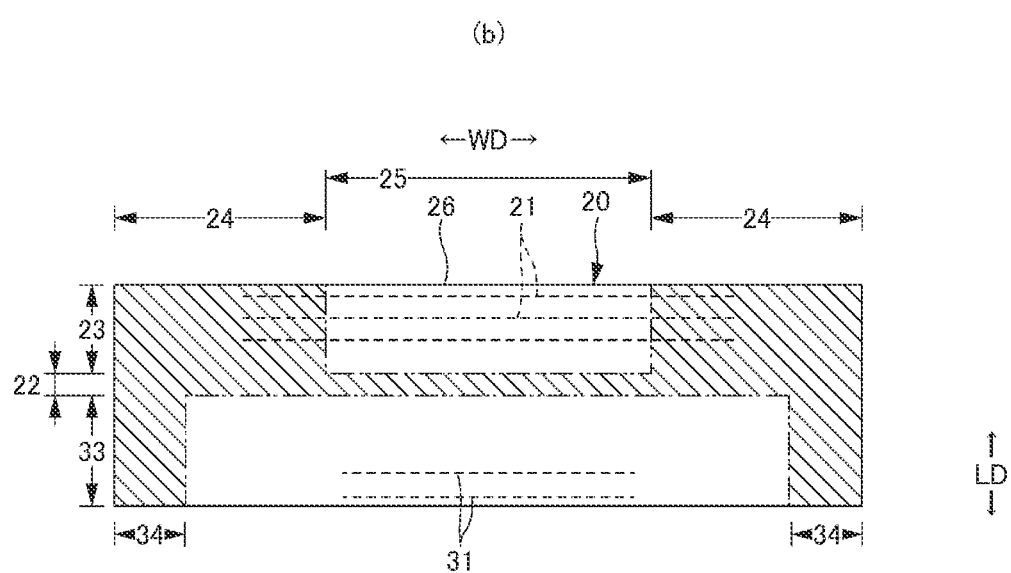

[FIG.6]
(a)
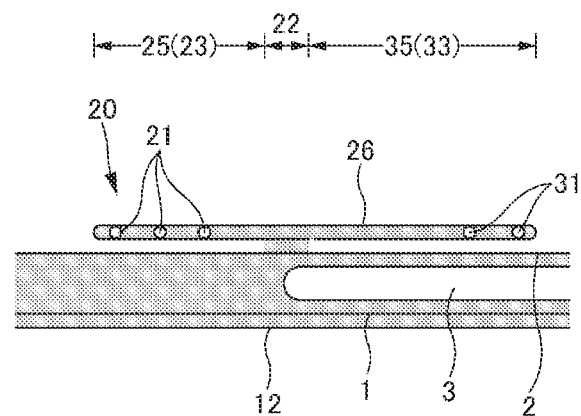
(b)
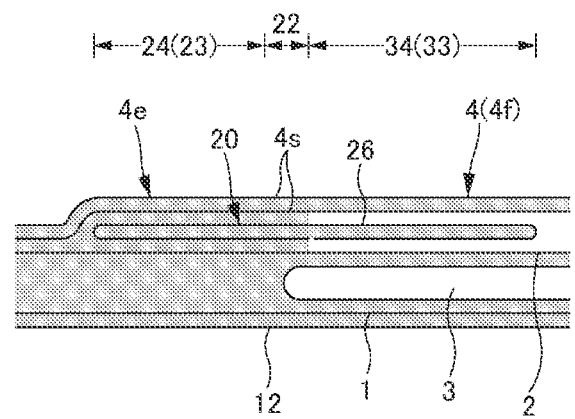

[FIG.7]
(a)
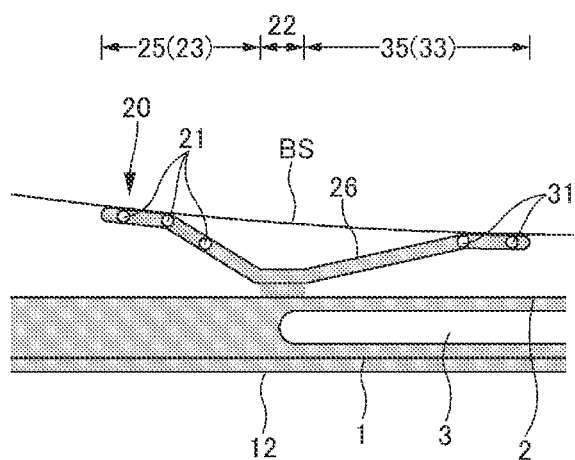
(b)
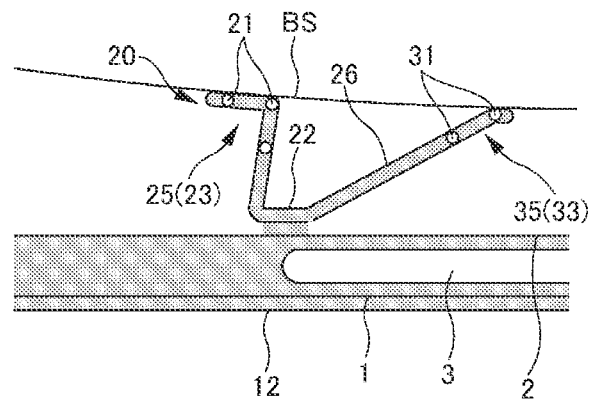

[FIG.8]
(a)
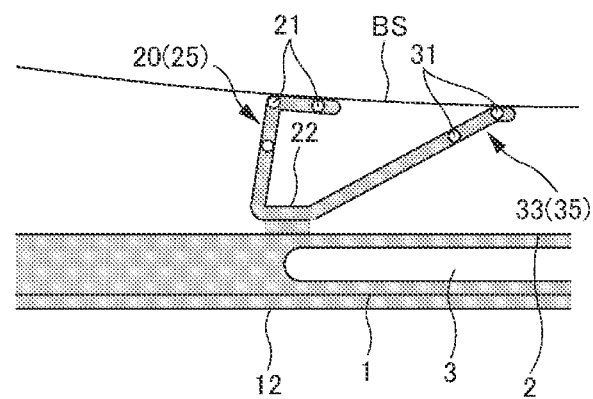
(b)
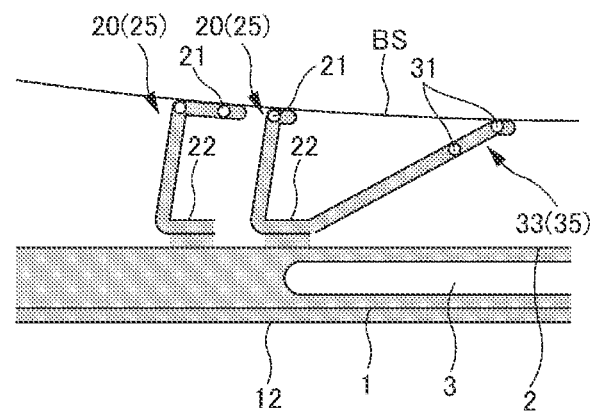

[FIG.9]
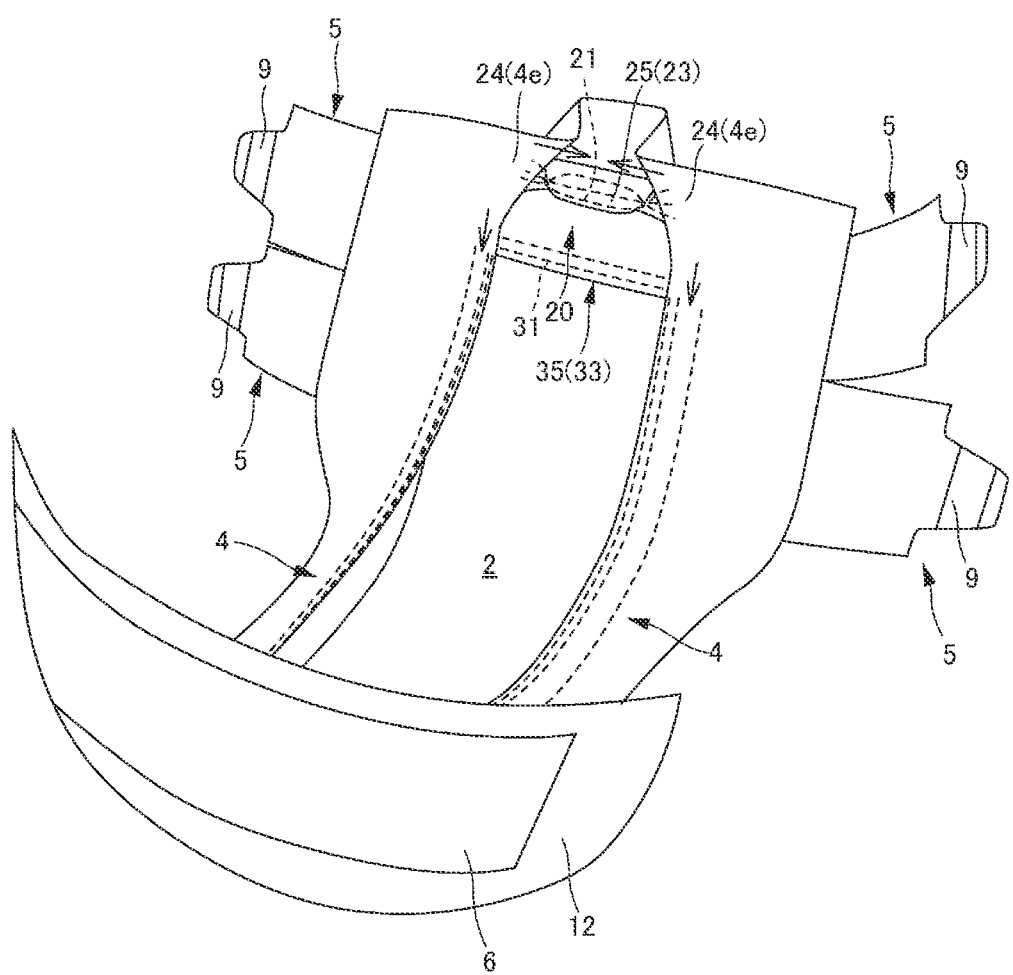

[FIG.10]
(a)
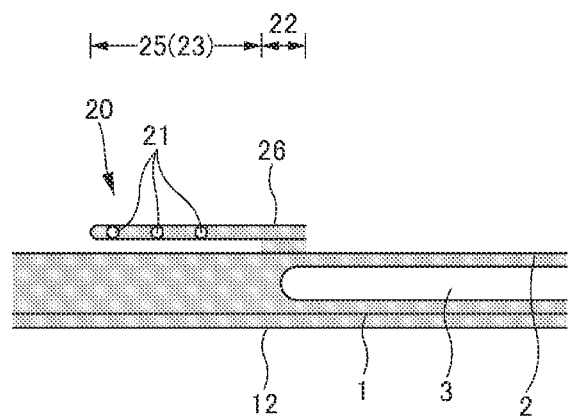
(b)
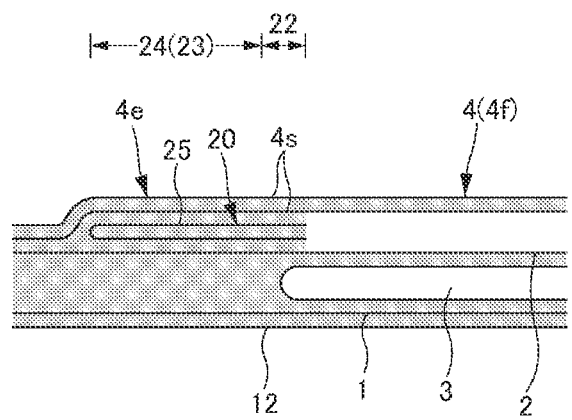

CONNECTING-TYPE DISPOSABLE WEARING ARTICLE

CROSS-REFERENCE TO RELATED APPLICATIONS

This application is the U.S. national stage application of International Application PCT/JP2021/010129, filed Mar. 12, 2021, which international application was published on Sep. 30, 2021, as International Publication WO 2021/193151 in the Japanese language. The International Application claims priority of Japanese Patent Application No. 2020-056600, filed Mar. 26, 2020. The international application and Japanese application are both incorporated herein by reference, in entirety.

TECHNICAL FIELD

The present invention relates to a connecting-type disposable wearing article.

BACKGROUND ART

In a connecting-type disposable wearing article, generally, three-dimensional side gathers rising toward a body side are provided on both sides in a width direction of a front surface so as to extend along a front-back direction, respectively (see for example, Patent Literatures 1 and 2). By providing such side gathers, excrement is retained between both the three-dimensional side gathers such that leakage particularly from peripheries of legs of a wearer is prevented.

The connecting-type disposable wearing article has generally poorer fitting in a lower torso direction than an underpants-type disposable diaper. Accordingly, in order to improve prevention of leakage from a dorsal side or from a ventral side, it is known that a waist stretchable region is provided, or that a three-dimensional waist gather rising toward the body side is provided along the width direction at a back side of rising portions of the three-dimensional side gathers (see for example, Patent Literature 1).

However, in a conventional connecting-type disposable wearing article, since a gap is likely to be generated in the back side of the rising portion of the three-dimensional side gather, there is a problem that when the excrement flows over the three-dimensional waist gather, the excrement leaks from a back end of a product (leakage from a back side or from a dorsal side).

In order to solve this problem, it has been considered that another three-dimensional waist gather is added at the back side of the rising portions of the three-dimensional side gathers. Nevertheless, there is still a problem also in this case that the three-dimensional waist gathers located at the back side are likely to rise insufficiently.

Meanwhile, such a problem is caused not only at the back side of a product but also at a front side of the product (leakage from a front side or from a ventral side).

CITATION LIST

Patent Literature

Patent Literature 1: JP 2010-22587 A
Patent Literature 2: JP 2016-32591 A

SUMMARY OF INVENTION

Technical Problem

Therefore, a main object of the present invention is to improve an effect of preventing leakage from a back side or from a front side in a connecting-type disposable wearing article.

Solution to Problem

A connecting-type wearing article that has solved the above problem is as follows.

<First Aspect>

A connecting-type wearing article including: a crotch portion having a center in a front-back direction;
a ventral side portion extending from the center in the front-back direction to a front side;
a dorsal side portion extending from the center in the front-back direction to a back side;
connecting portions provided in both side portions of the dorsal side portion and configured to be detachably connected to an external surface of the ventral side portion;
three-dimensional side gathers rising from a front surface are provided along first blocking positions disposed in both sides in a width direction,
each of the three-dimensional side gathers having a side root portion attached to an outside in the width direction of the first blocking position, a first portion extending from the side root portion, a first front fallen portion and a first back fallen portion formed by fixing a front end portion and a back end portion of the first portion in a fallen state, respectively, a first rising portion formed to be non-fixed between the first front fallen portion and the first back fallen portion in the first portion, and a first three-dimensional elastic member attached at least to a tip portion of the first rising portion, and
at least the tip portion of the first rising portion being contracted in the front-back direction together with the first three-dimensional elastic member and extensible in the front-back direction; and
a three-dimensional waist gather rising from the front surface is provided along a second blocking position disposed at least one of between both the first front fallen portions and between both the first back fallen portions,
the three-dimensional waist gather having a waist root portion attached along the second blocking position, a second portion extending from the waist root portion toward a waist edge side, second fallen portions formed by fixing both end portions in the width direction of the second portion in a fallen state, respectively, a second rising portion formed to be non-fixed between the second fallen portions in the second portion, and a second three-dimensional elastic member attached at least to a tip portion of the second rising portion, and
at least the tip portion of the second rising portion being contracted in the width direction together with the second three-dimensional elastic member and extensible in the width direction.

(Action and Effect)

The three-dimensional waist gather of the present article is characterized in that the second portion extends from the waist root portion toward the waist edge side, and in combination with this, the three-dimensional waist gather is disposed at least one of between both the first front fallen portions and between both the first back fallen portions.

That is, in the present three-dimensional waist gather, the second rising portion rises at the waist edge side thereof with respect to a crotch side thereof while the second fallen portions are pulled to each other as the second rising portion is contracted. On the other hand, in each of the three-dimensional side gathers, the first rising portion rises while the first front fallen portion and the first back fallen portion are pulled to each other as the first rising portion is contracted. Here, a region including the three-dimensional waist gather is disposed at least one of between both the first front fallen portions and between both the first back fallen portions. Therefore, when an action of each of the three-dimensional side gathers is performed by which the first front fallen portion and the first back fallen portion are pulled to each other, this action enables also the second portion of the three-dimensional waist gather to be pulled toward a waist root portion side. Further, a direction along which the first rising portion is contracted and a direction along which the second rising portion is contracted intersect to each other at each intersection site. Both intersection sites, namely, the first front fallen portions or the first back fallen portions, whichever dispose the three-dimensional waist gather interposed therebetween, are lifted toward a skin side of a wearer due to contraction in both the directions.

As a result, in the second rising portion of the three-dimensional waist gather, at a site where a gap is likely to be generated with respect to skin of the wearer, a rising situation of the second rising portion changes characteristically depending on a size of the gap. Specifically, as long as the above gap is small, a tip of the second rising portion of the three-dimensional waist gather is directed to the waist edge side and the second rising portion rises with a small angle to be brought into a surface-contact with the skin of the wearer. This means that in a state where a leakage risk is small, proper fitting can be secured with comfortable wearing feeling. On the other hand, as the gap is enlarged, the second rising portion of the three-dimensional waist gather rises high at a tip side thereof, in particular, when tightening of the wearing article around a lower torso of the wearer may be loosened, a middle portion in the width direction of the second rising portion rises high at the tip side thereof such that the tip side thereof is warped toward the crotch side, or even if it is not warped, it exhibits near behavior. In this way, in a state where the leakage risk is increased, an effect for preventing the leakage is enhanced in change of the rising situation. Conventionally, such change of the rising situation occurred at the three-dimensional waist gather has not been found. However, in the present three-dimensional waist gather, such change of the rising situation can prevent effectively leakage from the back side or leakage from the front side caused particularly by a wearing condition which is loosened over time (e.g., during meals).

<Second Aspect>

The connecting-type disposable wearing article according to the first aspect, wherein
   in a state where the wearing article is spread, the three-dimensional waist gather has the second three-dimensional elastic member located closer to a waist edge than the connecting portions.

(Action and Effect)

In the connecting-type disposable wearing article, a gap is likely to be generated between the skin and a region located closer to the waist edge than the connecting portions (in a case where each side of the wearing article has a plurality of connecting portions in the front-back direction, these connecting portions refer to those closest to the waist edge). Therefore, such connecting-type disposable wearing article is provided preferably with the above mentioned three-dimensional waist gather.

<Third Aspect>

The connecting-type disposable wearing article according to the first or the second aspect, wherein
   the three-dimensional waist gather has: a third portion extending from the waist root portion toward a crotch side; third fallen portions formed by fixing both end portions in the width direction of the third portion in a fallen state, respectively; a third rising portion formed to be non-fixed between the third fallen portions in the third portion; and a third three-dimensional elastic member attached at least to a tip portion of the third rising portion.

(Action and Effect)

The three-dimensional waist gather of the present aspect is characterized in that the third portion is provided at the crotch side of the second portion so as to rise while it extends in the opposite direction with respect to the second portion. In this way, the third portion basically blocks movement of excrement, but when a part of the excrement overflows the third portion for any reason, the second portion prevents the leakage thereof. That is, a function of preventing the leakage is performed in two stages. Here, as stated above, since a blocking effect of the second portion is basically different from that of the third portion, it is needless to say that the present aspect is more excellent in preventing the leakage than a wearing article where two identical rising portions which would be simply provided doubly.

<Fourth Aspect>

The connecting-type disposable wearing article according to any one of the first to third aspects, wherein
   the second three-dimensional elastic member is a plurality of second three-dimensional elastic members provided at intervals in the front-back direction, and
   a stretch rate of each of the second three-dimensional elastic members in a state where the wearing article is spread decreases toward the waist edge side.

(Action and Effect)

It is preferable that the plurality of second three-dimensional elastic members having different stretch rates are provided as in the present aspect, because it becomes likely to be easier for the tip side of the second rising portion to be warped.

ADVANTAGEOUS EFFECTS OF INVENTION

According to the present invention, for example, an effect of preventing the leakage from the back side or the leakage from the front side in the connecting-type disposable wearing article can be improved advantageously.

BRIEF DESCRIPTION OF DRAWINGS

FIG. 1 is a plan view illustrating an internal surface of a tape-type disposable diaper in a state where the diaper is spread.

FIG. 2 is a plan view illustrating an external surface of a tape-type disposable diaper in a state where the diaper is spread.

FIG. 3 is a cross-sectional view cut along iii-iii of FIG. 1.

FIG. 4 is a cross-sectional view cut along iv-iv of FIG. 1.

FIG. 5(*a*) is an enlarged view of a main part of FIG. 1, and FIG. 5(*b*) is an enlarged view of a main part of a three-dimensional waist gather.

FIG. 6(a) is a cross-sectional view cut along v-v of FIG. 1 and FIG. 6(b) is a cross-sectional view cut along vi-vi of FIG. 1

FIG. 7 is a cross-sectional view of a main part of a tape-type disposable diaper in a state where the diaper is worn.

FIG. 8 is a cross-sectional view of a main part of a tape-type disposable diaper in a state where the diaper is worn.

FIG. 9 is a perspective view of a tape-type disposable diaper illustrating a state where the diaper has a substantially natural length before the diaper is used.

FIG. 10 is a cross-sectional view of a main part of another example of a tape-type disposable diaper in a state where the diaper is spread.

DESCRIPTION OF EMBODIMENTS

FIGS. 1 to 6 illustrate a tape-type disposable diaper as an example of a connecting-type disposable wearing article. Note that among hot melt adhesives applied portions, some of them requiring explanations are indicated by hatch patterns and dot patterns in plan views and dot patterns in cross-sectional views, respectively. The hot melt adhesive can be applied by a known method such as slot application, bead application into a continuous line or dot shape, spray application into a spiral shape, a Z shape, or pattern coating (transfer of a hot melt adhesive by a letterpress method). Alternatively or in addition, in a fixed portion of an elastic member, the hot melt adhesive can be applied to an external peripheral surface of the elastic member, and the elastic member can be fixed to an adjacent member. Examples of the hot melt adhesive include an EVA-based agent, a pressure sensitive adhesive rubber-based agent (elastomer-based agent), a polyolefin-based agent, and a polyester/polyamide-based agent, and these can be used without particular limitation. As a bonding means for bonding components to each other, a means by material welding such as heat sealing or ultrasonic sealing can also be used.

The tape-type disposable diaper has: a crotch portion disposed so as to include a center LC in a front-back direction LD; a ventral side portion F extending to a front side of the center LC in the front-back direction LD; a dorsal side portion B extending to a back side of the center LC in the front-back direction LD. Further, this tape-type disposable diaper has: an absorber 3 contained in a range including the crotch portion; a liquid pervious top sheet 2 covering a front surface side of the absorber 3; a liquid impervious sheet 1 covering a back surface side of the absorber 3; and an exterior nonwoven fabric 12 covering a back surface side of the liquid impervious sheet 1 and forming an external surface of a product.

Hereinafter, a material and a characteristic part of each portion will be described in due order.

(Absorber)

A basic structure of absorber 3 has a single layer or a plurality of layers of fiber assembly. As the fiber assembly, accumulated pulp fibers, a filament assembly of cellulose acetate or the like, or a nonwoven fabric can be used. The absorber 3 as necessary can contain super absorbent polymer in the form of particles or the like. The particles or the like of the super absorbent polymer can be mixed with fibers in the layer of fiber assembly or can be fixed to the fibers in the layer of fiber assembly or fixed to a surface of the layer of fiber assembly. Alternatively, a layer of the super absorbent polymer can be interposed between the layers of fiber assembly. The absorber 3 as necessary can be wrapped with a wrapping sheet (not illustrated) such as crepe paper or the like. Although the shape of the absorber 3 can be appropriately determined, it is preferable that the absorber 3 has a shape extending from the front side of the crotch portion to the back side thereof like a rectangular shape, in addition to an hourglass shape (a narrowing shape) having a narrower portion with a narrower width than the front and back side thereof in an intermediate portion including the crotch portion in the front-back direction LD as illustrated in the drawings. The absorber 3 can have a fiber basis weight of about 100 to 500 g/m$^2$ and a thickness of about 1 to 15 mm. In addition, the super absorbent polymer in the absorber 3 can have a basis weight of about 0 to 300 g/m$^2$.

(Liquid Impervious Sheet)

The liquid impervious sheet 1 is provided for blocking oozing of excrement on a back surface of the product. As the liquid impervious sheet 1, a plastic film such as a polyethylene film can be used. Additionally, a sheet having moisture permeability without losing water blocking ability can be used from a viewpoint of preventing stuffiness. As this liquid impervious and moisture permeable sheet, a microporous sheet can be used which is obtained by kneading an inorganic filler in a polyolefin-based resin such as polyethylene or polypropylene, molding the kneaded mixture into a sheet, and stretching the sheet in one or two axial directions.

It is desirable that the liquid impervious sheet 1 extends within the same range as or a wider range than that of the absorber 3 in the front-back direction LD and a width direction WD. However, for example, when another water blocking means is present, as another possible configuration, an end portion of the absorber 3 does not have to be covered with the liquid impervious sheet 1 in the front-back direction LD or the width direction WD as necessary.

In order to make an external surface of the diaper have a cloth-like appearance and touch, a whole back surface of the liquid impervious sheet 1 can be covered with the exterior nonwoven fabric 12. The exterior nonwoven fabric 12 can be omitted, and in this case, the liquid impervious sheet 1 forms the external surface of the product.

(Top Sheet)

The top sheet 2 is liquid permeable, and examples thereof include a perforated or imperforated nonwoven fabric and a porous plastic sheet.

The top sheet 2 extends from a front end to a back end of the product in the front-back direction LD and extends to the lateral sides in the width direction WD beyond the absorber 3. However, for example, when lines, from which three-dimensional side gathers 4 described later start to rise, are closer to the center in the width direction WD than side edges of the absorber 3, appropriate deformation can be made, for example, the width of the top sheet 2 is made shorter than the maximum width of the absorber 3 as necessary.

(Side Flap)

The tape-type disposable diaper in the illustrated example has a pair of side flaps SF without the absorber 3 on the lateral sides of the absorber 3, respectively. As in the illustrated example, each of the side flaps SF can be formed of a material which is continuous from a portion including the absorber 3 (the exterior nonwoven fabric 12 or the like). Alternately, each of the side flaps SF can be formed by attaching another material to the portion including the absorber 3.

(Planar Gather)

In intermediate portions of the side flaps SF in the front-back direction LD, elongated leg periphery elastic members 7 are fixed with a hot melt adhesive or the like in a state of being extended along the front-back direction LD between the liquid impervious sheet 1 and the exterior nonwoven fabric 12, respectively. Then, due to the contraction of the leg periphery elastic members 7, so-called planar gathers are formed in the side flaps SF, respectively. These planar gathers make side portions of the diaper elastically stretchable such that the side portions fit around legs. The leg periphery elastic members 7 may curve around the legs.

Number of the leg periphery elastic members 7 in the right and left side portions can be appropriately determined. However, the number of the leg periphery elastic member 7 in each side portion is preferably about 1 to 10, more preferably about 3 to 8. In a case of a plurality of leg periphery elastic members, they are preferably arranged at intervals of about 2 to 15 mm, more preferably about 6 to 10 mm. As a material of each leg periphery elastic member 7, commonly used material such as styrene-based rubber, olefin-based rubber, urethane-based rubber, ester-based rubber, polyurethane, polyethylene, polystyrene, styrene-butadiene, silicone, polyester or the like formed to be thread-shaped, string-shaped, belt-shaped or the like. The fineness of the leg periphery elastic member 7 is preferably about 500 to 1500 dtex. In a case where a material of each leg periphery elastic member is natural rubber, the cross-sectional area thereof is preferably about 0.1 to 3 $mm^2$, more preferably about 0.5 to 3 $mm^2$. Further, a stretch rate of each leg periphery elastic member 7 when it is fixed is preferably about 150 to 250%.

(Wing Portion)

In the present tape-type disposable diaper, the dorsal side portion B has wing portions each of which extends outward in the width direction WD beyond the width of the crotch portion. Similarly, the ventral side portion F has also wing portions each of which extends outward in the width direction WD beyond the width of the crotch portion. These wing portions can be formed of a different material from those of other portions. However, as in the illustrated example, in the diaper configured to be provided with the side flaps SF, it is preferable that leg periphery edges Le, which are depressed inward and continuous along side edges of the crotch portion to reach lower edges of portions to be the wing portions, are formed by cutting intermediate portions in the front-back direction LD of side portions of the side flaps SF, respectively, because the wing portions can be manufactured easily in this way.

(Connecting Tape)

Connecting tapes 5 are attached to side edges of both the side portions (in the illustrated example, the wing portions of the side flaps SF) of the dorsal side portion B so as to project therefrom, respectively. In addition, a target sheet 6 is adhered to a surface of a lower torso portion in the ventral side portion F so as to extend along the width direction WD. At the time of attaching the diaper to a body, in a state where the diaper is applied to the body, both the connecting tapes 5 are turned from both sides of a waist to an external surface of the ventral side portion F to be connected to the target sheet 6. The target sheet 6 can be omitted, and in this case, the connecting tapes 5 are directly connected to the external surface of the diaper (in the illustrated example, the exterior nonwoven fabric 12).

As illustrated in FIG. 3, each connecting tape 5 has: an attachment portion 5f fixed with a means such as a hot melt adhesive between sheets of a waist side portion of the side flap SF in the dorsal side portion B; and a projecting portion 5e projecting outward in the width direction WD from between the sheets at a side edge of the side flap SF. The projecting portion 5e has: a tip end 5p; and a main unit portion 5b closer to a base edge than the tip end 5p. To an internal surface of the tip end 5p of each connecting tape 5, a hook material (male member) of a mechanical fastener (hook and loop fastener) is attached as a connecting portion 9 for being connected to the target sheet 6. The hook material has a large number of hook-shaped projections on a surface thereof. In addition, as the target sheet 6, a sheet is attached to the external surface of the ventral side portion F and this sheet has a surface (female member of a mechanical fastener (hook and loop fastener)) to which the hook-shaped projections are detachably engaged. Instead of the target sheet 6, a material itself of the external surface of the diaper can be used. Further, instead of the hook material, an adhesive material layer can be used as the connecting portion 9, and in this case, as the target sheet 6, a resin tape having a smooth surface to which the adhesive material layer can be adhered easily can be used.

In addition, as illustrated in FIG. 1, in each of the connecting tapes 5, a perforated line 10 is provided along the width direction WD so as to extend in an intermediate portion in the front-back direction LD of the main unit portion 5b from an outside edge in the width direction WD thereof. Then, as illustrated in FIG. 9, the connecting tapes 5 are torn along the perforated lines 10 such that the connecting tapes 5 can be divided to upper portions and lower portions, respectively. Then each of the upper portion and the lower portion includes an attachment portion, a main unit portion, a tip end and a connecting portion 9. Instead of the perforated lines 10, it is possible that the connecting tapes 5 are originally separated by cutting or the like. In each of such connecting tapes 5, the upper portion thereof and the lower portion thereof are detachably connected to the target sheet 6 of the ventral side portion F while the upper portion and the lower portion are crossed to each other. Of course, the connecting tape 5 is not limited to this type of tape which is divided into the upper and lower two portions, and other known types, for example a tape which is not divided into two portions, can be used.

(Three-Dimensional Side Gather)

As illustrated in FIGS. 1, 4 and 6, in order to prevent so-called side leakage by blocking movement of the excrement transmitted laterally on the top sheet 2, in both the side portions in the width direction WD on the front surface, three-dimensional side gathers 4 rising from the front surface are provided along first blocking positions extending in the front-back direction.

More specifically, each of the three-dimensional side gathers 4 has: a side root portion 4x fixed in a region including the side flap SF; a first portion 4c extending from the side root portion 4x; a first front fallen portion 4b and a first back fallen portion 4e formed by fixing a front end portion and a back end portion of the first portion 4c in a fallen state, respectively; a first rising portion 4f formed to be non-fixed between the first front fallen portion 4b and the first back fallen portion 4e in the first portion 4c. In addition, a first three-dimensional elastic member 4G is attached at least to a tip portion of the first rising portion 4f.

Each member of the three-dimensional side gather 4 is formed of a three-dimensional side sheet 4s. This three-dimensional side sheet 4s is two-folded at a tip (an end being opposite to a side root portion 4x) of the first portion 4c to form a two-layered structure whose range includes the non-fixed free portion. The first three-dimensional elastic member 4G is interposed between two layers of this two-layered structure. The first three-dimensional elastic member 4G may be provided only in the first rising portion 4f. However, it is preferable that, as in the illustrated example, the first three-dimensional elastic member 4G is fixed in a range from a back end portion of the first front fallen portion 4b to a front end portion of the first back fallen portion 4e, because a contraction force of the first three-dimensional elastic member 4G is acted not only in the whole of the first rising portion 4f but also in the back end portion of the first front fallen portion 4b and in the front end portion of the first back fallen portion 4e.

An internal surface of the three-dimensional side sheet 4s has a fixed start point in the width direction WD on a side portion of the top sheet 2, and that portion of the three-dimensional side sheet 4s, which is located at an outside in the width direction WD of the fixed start point, is fixed with a hot melt adhesive or the like to an internal surface of each side flap SF, namely in the illustrated example, a side portion of the liquid impervious sheet 1 and a side portion of the exterior nonwoven fabric 12, which is located at an outside in the width direction WD of the side portion of the liquid impervious sheet 1. Note that dotted pattern portions in each of the plan views indicate fixed portions of three-dimensional side gather 4.

That portion of the three-dimensional side gather 4, which is located at an inside in the width direction WD of the fixed start point, is fixed to the top sheet 2 at both end portions in the front-back direction. However, the first rising portion 4f therebetween is the non-fixed free portion. Accordingly, the first rising portion 4f rises while it is contracted in the front-back direction due to the contraction force of the first three-dimensional elastic member 4G. In addition, the first rising portion 4f is extensible in the front-back direction. Therefore, the first rising portion 4f fits closely to a surface of the body. Further, as the first rising portion 4f is contracted in the front-back direction due to the contraction force of the first three-dimensional elastic member 4G, a portion including the first front fallen portion 4b and a portion including the first back fallen portion 4e are deformed so as to close to each other.

Although not illustrated, as is well known, both end portions in the front-back direction LD of the first portion 4c of the three-dimensional side gather 4 can be fixed as the fallen portions in a two-folded state having a base edge side portion extending inward in the width direction WD from an outside portion in the width direction WD and a tip side portion folded back to a body side from an end edge of the base edge side portion on the central side in the width direction WD and extending outward in the width direction WD.

A kind of the three-dimensional side sheet 4s is not particularly limited. However usually, in order to secure a liquid barrier property, a water-repellent sheet is used. In particular, a nonwoven fabric having a meltblown layer sandwiched between spunbond layers (an SMS nonwoven fabric, an SMMS nonwoven fabric, an SSMS nonwoven fabric, or an SSMMS nonwoven fabric) is suitable from a viewpoint of achieving both the texture and the liquid barrier property. In addition to using a single piece of nonwoven fabric, it is also possible to use stacked multiple nonwoven fabrics. In the latter case, the nonwoven fabrics are preferably bonded to each other with a hot melt adhesive or the like.

For a material of the first three-dimensional elastic member 4G, natural rubber or synthetic rubber formed to be thread-shaped, string-shaped, belt-shaped or the like can be used. Specifically, commonly used one such as polystyrene-based rubber, polyolefin-based rubber, polyurethane-based rubber, polyester-based rubber, polyurethane, polyethylene, polystyrene, styrene-butadiene copolymer, silicone, polyester or the like can be used. As illustrated in FIGS. 1 and 2, a plurality of the first three-dimensional elastic members 4G may be disposed on each side, or one first three-dimensional elastic member 4G may be disposed on each side. Further, a stretch rate of the first three-dimensional elastic member 4G in a state where the diaper is spread can be appropriately determined, but for example, it is possible to be about 230 to 270% in a case where the first three-dimensional elastic member 4G is a spandex thread rubber having the fineness of about 420 to 1120 dtex.

(End Flap)

The present tape-type disposable diaper has a pair of end flaps EF on a front side and a back side of the absorber 3, respectively, which do not include the absorber 3. The constituent members of the end flap EF change depending on the structure of the diaper. In the illustrated example, the end flap EP is formed by stacking a portion of the liquid impervious sheet 1, a portion of the exterior nonwoven fabric 12, a portion of the top sheet 2 and a portion of the three-dimensional side sheet 4s, which extend to the front side or the back side of the absorber 3, to be bonded to one another, but not limited thereto. The end flaps EF may be formed by adding sheets, which are dedicated for forming the end flaps EF, to the front side and the back side of the absorber 3, respectively.

Usually, the size of end flap EF in the front-back direction LD can be about 20 to 25% of the maximum length of the diaper in the front-back direction LD.

(Three-Dimensional Waist Gather)

On the other hand, as illustrated in FIGS. 1, 5 and 6, in a back end portion (in the illustrated example, end flap EF) of the disposable diaper in the illustrated example, a three-dimensional waist gather 20 rising from the front surface is provided along a second blocking position disposed between the first back fallen portions 4e. More specifically, as illustrated also in FIGS. 5 and 6, the three-dimensional waist gather 20 has: a waist root portion 22 attached along the second blocking position disposed in the end flap EF; a second portion 23 extending from the waist root portion 22 toward a waist edge side; second fallen portions 24 formed by fixing both end portions in the width direction WD of the second portion 23 in a fallen state, respectively; and a second rising portion 25 formed to be non-fixed between the second fallen portions 24 in the second portion 23. In addition, a second three-dimensional elastic member 21 is attached at least to a tip portion (an end portion on the waist edge side) of the second rising portion 25.

In addition, the three-dimensional waist gather 20 in the illustrated example is formed of a three-dimensional waist sheet 26. The three-dimensional waist sheet 26 is two-folded so as to form a two-layered structure in the three-dimensional waist gather 20. The second three-dimensional elastic member 21 is interposed and fixed with a hot melt adhesive or the like between two layers of a portion having this two-layered structure. The second three-dimensional elastic member 21 may be provided only in the second rising portion 25. However, it is preferable that the second three-dimensional elastic member 21 is provided in a range from a second fallen portion 24 on one side to a second fallen portion 24 on the other side, because the contraction force of the second three-dimensional elastic member 21 is acted not only in the whole of the second rising portion 25 but also in the second fallen portions 24.

An internal surface of the three-dimensional waist sheet 26 in an illustrated example has a fixed start point in the front-back direction LD on the end flap EF, and that portion of the three-dimensional waist sheet 26, which is located at a back side of the fixed start point, is fixed with a hot melt adhesive or the like to an internal surface of the end flap EF, namely, in the illustrated example, a front surface of the top sheet 2. Note that a fixed portion of the three-dimensional waist sheet 26 to the top sheet 2 is indicated in FIGS. 1 and 5(a) by a hatch pattern in which southeast-pointing oblique lines are drawn.

That portion of the three-dimensional waist gather 20, which is located closer to a waist edge than the fixed start point, is fixed to the top sheet 2 at both end portions in the width direction WD as the second fallen portions 24. However, the second rising portion 25 therebetween is the non-fixed free portion. Accordingly, the second rising portion 25 rises while it is contracted in the width direction WD due to the contraction force of the second three-dimensional elastic member 21. In addition, the second rising portion 25 is extensible in the width direction WD. Therefore, the second rising portion 25 fits closely to the surface of the body. Further, as the second rising portion 25 is contracted in the width direction WD due to the contraction force of the second three-dimensional elastic member 21, a portion including one of the second fallen portions 24 and a portion including the other of the second fallen portions 24 are deformed so as to close to each other.

On the other hand, in each of the three-dimensional side gathers 4, the first rising portion 4f rises while the first fallen portion 4b and the first back fallen portion 4e are pulled to each other as the first rising portion 4f is contracted. Here, a region including the three-dimensional waist gather 20 is disposed between both the first back fallen portions 4e. Therefore, when an action of each of the three-dimensional side gathers 4 is performed by which the first front fallen portion and the first back fallen portion 4e are pulled to each other (see arrows in FIG. 9), this action enables also the second portions 23 of the three-dimensional waist gather 20 to be pulled toward a waist root portion 22 side (see arrows in FIG. 9). Further, a direction along which the first rising portion 4f is contracted and a direction along which the second rising portion 25 is contracted intersect to each other at each intersection site. Both intersection sites, namely, the first front fallen portions or the first back fallen portions 4e, whichever dispose the three-dimensional waist gather 20 interposed therebetween, are lifted toward a skin side of a wearer due to contraction in both the directions.

As a result, in the second rising portion 25 of the three-dimensional waist gather 20, at a site where a gap is likely to be generated with respect to the skin of the wearer, as illustrated in FIGS. 7(a), 7(b) and 8(a), a rising situation of the second rising portion 25 changes characteristically depending on a size of the gap generated between an internal surface of the product and a skin surface BS of the wearer. Specifically, as long as the above gap is small, as illustrated in FIG. 7(a), a tip of the second rising portion 25 of the three-dimensional waist gather 20 is directed to the waist edge side and the second rising portion 25 rises with a small angle to be brought into a surface-contact with the skin surface BS of the wearer. This means that in a state where a leakage risk is small, proper fitting can be secured with comfortable wearing feeling. On the other hand, as the gap is enlarged, as illustrated in FIG. 7(b), the second rising portion 25 of the three-dimensional waist gather 20 rises high at a tip side thereof, in particular, when tightening of the diaper around a lower torso of the wearer may be loosened, as illustrated in FIGS. 8(a) and 9, a middle portion in the width direction WD of the second rising portion rises high at the tip side thereof such that the tip side thereof is warped toward the crotch side (or even if it is not warped, it exhibits near behavior). In this way, in a state where the leakage risk is increased, an effect for preventing the leakage is enhanced in change of the rising situation. Conventionally, such change of the rising situation occurred at the three-dimensional waist gather 20 has not been found. However, in the present three-dimensional waist gather, such change of the rising situation can prevent effectively leakage from a back side or leakage from a front side caused particularly by a wearing condition which is loosened over time (e.g., during meals).

Each of the second fallen portions 24 in the illustrated example is a portion which is interposed between the top sheet 2 and the three-dimensional side sheet 4s in the first back fallen portion 4e and bonded to both the sheets with a bonding means such as a hot melt adhesive. However, each of the second fallen portions 24 may be provided on the three-dimensional side sheet 4s in the first back fallen portion 4e. That is, although not illustrated, the three-dimensional waist gather 20 may be provided, at both the second fallen portions 24 thereof, on both the three-dimensional side gathers 4.

A kind of the three-dimensional waist sheet 26 is not particularly limited. However usually, in order to secure a liquid barrier property, a water-repellent sheet is used. In particular, a nonwoven fabric having a meltblown layer sandwiched between spunbond layers (an SMS nonwoven fabric, an SMMS nonwoven fabric, an SSMS nonwoven fabric, or an SSMMS nonwoven fabric) is suitable from a viewpoint of achieving both the texture and the liquid barrier property. In addition to using a single piece of nonwoven fabric, it is also possible to use stacked multiple nonwoven fabrics. In the latter case, the nonwoven fabrics are preferably bonded to each other with a hot melt adhesive or the like.

For a material of the second three-dimensional elastic member 21, natural rubber or synthetic rubber formed to be thread-shaped, string-shaped, belt-shaped or the like can be used. Specifically, commonly used one such as styrene-based rubber, olefin-based rubber, urethane-based rubber, ester-based rubber, polyurethane, polyethylene, polystyrene, styrene-butadiene, silicone, polyester or the like can be used. As in the illustrated example, a plurality of the second three-dimensional elastic members 21 may be disposed on each side, or one second three-dimensional elastic member 21 may be disposed on each side. Further, a stretch rate of the second three-dimensional elastic member 21 in the state where the diaper is spread can be appropriately determined, but for example, it is preferably about 130 to 250%, more preferably 160 to 200% in a case where the second three-dimensional elastic member 21 is a spandex thread rubber having the fineness of about 600 to 1300 dtex.

In a case where a plurality of the second three-dimensional elastic members 21 are provided at intervals in the front-back direction LD, these members may have the same stretch rate. However, a part or all of these members can have different stretch rates. For example, it is preferable that the stretch rate of each of the second three-dimensional elastic members 21 in the state where the diaper is spread decreases toward the waist edge side, because it becomes likely to be easier for the tip side of the second rising portion 25 to be warped.

Arrangement of the second three-dimensional elastic member 21 can be appropriately determined. However, if the second three-dimensional elastic member 21 located in the tip portion (closest to the waist edge) is away from a back edge of the waist root portion 22 by about 2 to 40 mm, it becomes likely to be easier for the tip side of the second rising portion 25 to be warped, which is preferable. Similarly, the second three-dimensional elastic member 21 located in the tip portion (closest to the waist edge) is preferably away from a front edge of the end flap EF, because of the same reason.

In the tape-type disposable diaper, a gap is likely to be generated between the skin and a region located closer to the waist edge than the connecting portions 9 (in a case where each side of the tape-type disposable diaper has a plurality of connecting portions in the front-back direction LD, these connecting portions refer to those closest to the waist edge).

Therefore in the state where the diaper is spread, it is preferable that the three-dimensional waist gather 20 has the second three-dimensional elastic member 21 located closer to the waist edge than the connecting portions 9, because the deforming of the three-dimensional waist gather 20 explained above becomes to be exhibited effectively.

As an example illustrated in FIGS. 6 to 8, it is also preferable that the three-dimensional waist gather 20 has: a third portion 33 extending from the waist root portion 22 toward a crotch side; third fallen portions 34 formed by fixing both end portions in the width direction WD of the third portion 33 in a fallen state, respectively; a third rising portion 35 formed to be non-fixed between the third fallen portions 34 in the third portion 33; and a third three-dimensional elastic member 31 attached at least to a tip portion of the third rising portion 35. In this way, the third portion 33 basically blocks movement of the excrement, but when a part of the excrement overflows the third portion 33 for any reason, the second portion 23 prevents the leakage thereof. That is, a function of preventing the leakage is performed in two stages. Here, as stated above, since a blocking effect of the second portion 23 is basically different from that of the third portion 33, it is needless to say that this example is more excellent in preventing the leakage than a diaper where two identical rising portions which would be simply provided doubly against the leakage.

Of course, as illustrated in FIG. 10, the third portion 33 can be omitted. In addition, as in an example illustrated in FIG. 8(b), a plurality of the second portions 23 can be provided at intervals in the front-back direction LD.

In the illustrated example, the third portion 33 of the three-dimensional waist gather is, in the front-back direction LD, located in ranges including the first rising portions 4f of the three-dimensional side gathers 4. However, a part or all of the third portion 33 is, in the front-back direction LD, located in ranges including the first fallen portions. In the former case, the third fallen portions 34 are located in ranges including the side root portions 4x, while in the latter case, the third fallen portions 34 may be located in ranges including the first back fallen portions 4e.

In addition, in a case where the third portion 33 of the three-dimensional waist gather is, in the front-back direction LD, located in ranges including the first rising portions 4f of the three-dimensional side gathers 4, it is preferable that the third rising portion 35 and each of the first rising portions 4f are not bonded to each other in a portion where they are overlapped. However, it is possible that they are bonded to each other in the portion where they are overlapped.

<Others>

In the above examples, the three-dimensional waist gather 20 is provided only in the dorsal side portion B. However, alternatively or in addition, the three-dimensional waist gather 20 can be provided also in the ventral side portion F. This means that the three-dimensional waist gather 20 can be at least one of between the first front fallen portions 4b and between the first back fallen portions 4e.

As a nonwoven fabric in the above description, a known nonwoven fabric can be appropriately used according to a site or a purpose. Examples of a constituent fiber of the nonwoven fabric include, but are not limited to, a synthetic fiber such as a polyolefin-based fiber including polyethylene and polypropylene, a polyester-based fiber, or a polyamide-based fiber (including a composite fiber such as core-sheath in addition to a single component fiber), a regenerated fiber such as rayon or cupra, and a natural fiber such as cotton. These fibers can be mixed and used. In order to enhance flexibility of the nonwoven fabric, it is preferable to use a crimped fiber as the constituent fiber. In addition, the constituent fiber of the nonwoven fabric may be a hydrophilic fiber (including a fiber that has become hydrophilic by a hydrophilizing agent), a hydrophobic fiber, or a water-repellent fiber (including a fiber that has become water-repellent by a water repellent agent). In addition, the nonwoven fabric is generally classified into a short fiber nonwoven fabric, a long fiber nonwoven fabric, a spunbonded nonwoven fabric, a meltblown nonwoven fabric, a spunlace nonwoven fabric, a thermal bond (air through) nonwoven fabric, a needle punch nonwoven fabric, a point bond nonwoven fabric, a laminated nonwoven fabric (an SMS nonwoven fabric, an SMMS nonwoven fabric, or the like having a meltblown layer sandwiched between spunbond layers), and the like depending on a fiber length, a sheet forming method, a fiber bonding method, and a stacked structure, and any of these nonwoven fabrics can be used.

<Description of Terms Used in Specification>

The following terms used in the specification should be understood to have the meanings defined below unless otherwise specified in the specification.

"Front-back direction" means a direction (longitudinal direction) indicated by a reference character LD in the drawing, "width direction" means a direction (left-right direction) indicated by a reference character WD in the drawing, and the front-back direction and the width direction are orthogonal to each other.

"Machine direction: MD" and "cross direction: CD" mean the flow direction (MD) in a manufacturing equipment and the lateral direction (CD) orthogonal to the flow direction, and either one is the front-back direction and the other is the width direction depending on each member of a product. The MD of a nonwoven fabric is the direction of fiber orientation of the nonwoven fabric. The fiber orientation is a direction along which a fiber of a nonwoven fabric runs and determined by, for example, a measurement method in accordance with the fiber orientation test method based on the zero distance tensile strength of TAPPI standard method T481 or a simple measurement method for determining the fiber orientation direction from the tensile strength ratio of the front-back direction and the width direction.

"Front surface side" means a side closer to a wearer's skin when an article is worn. "Back surface side" means a side far from a wearer's skin when an article is worn. "Front surface" means a surface of a member closer to a wearer's skin when an article is worn. "Back surface" means a surface far from a wearer's skin when an article is worn.

"Stretch rate" means a value obtained when a natural length is set to 100%. For example, the stretch rate of 200% has the same meaning as the elongation ratio of 2.

"Gel strength" is measured as follows. 1.0 g of super absorbent polymer is added to 49.0 g of artificial urine (prepared by mixing 2 wt % of urea, 0.8 wt % of sodium chloride, 0.03 wt % of calcium chloride dihydrate, 0.08 wt % of magnesium sulfate heptahydrate, and 97.09 wt % of ion exchanged water), and the resulting mixture is agitated with a stirrer. The resulting gel is left in a thermo-hygrostat at 40° C.×60% RH for three hours and then cooled to room temperature. The gel strength of the gel is measured with a curdmeter (Curdmeter-MAX ME-500 manufactured by I. Techno Engineering Co., Ltd.)

"Basis weight" is measured as follows. After preliminary drying of a sample or a test piece, the sample or the test piece is left in a test room or a test device under normal conditions (an ambient temperature of 23±1° C. and with a relative humidity of 50±2% at the testing site) until the weight of sample or test piece reaches constant mass. Preliminary drying is to achieve the constant mass of the sample or test piece under an environment having a temperature of 100° C. For fibers having a standard moisture regain of 0.0%, preliminary drying may be omitted. The test piece having the constant mass is cut with a cutting template having the size of 100 mm×100 mm into samples having the size of 100 mm×100 mm. The weight of the sample is measured. The measured weight is multiplied by 100 to determine the weight per one square meter, which is defined as the basis weight.

"Thickness" is automatically measured with an automatic thickness gauge (KES-G5 handy compression tester) under a load of 0.098 N/cm$^2$ and a pressurized area of 2 cm$^2$. The thickness of perforated nonwoven fabric is measured at a portion other than the holes or projections around the holes.

"Water absorption capacity" is measured in accordance with JIS K7223-1996 "Testing method for water absorption capacity of super absorbent polymers".

"Water absorption rate" is defined as "time that elapses before the end point" measured with 2 g of super absorbent polymers and 50 g of normal saline solution in accordance with JIS K7224-1996 "Testing method for water absorption rate of super absorbent polymers".

"State where an article is spread" means a state where the article is spread flat without contraction or slackness.

The size of each component means a size in a state where an article is spread, not in a state where the article has a natural length, unless otherwise specified.

The tests and measurements are carried out in a laboratory or apparatus under normal conditions (a temperature of 23±1° C. and a relative humidity of 50±2% at the testing site), unless the environmental condition for the tests and measurements are otherwise specified.

INDUSTRIAL APPLICABILITY

The present invention is applicable to connecting-type disposable wearing articles such as tape-type disposable diapers as in the above examples.

REFERENCE SIGNS LIST

1 Liquid impervious sheet
10 Perforated line
2 Top sheet
3 Absorber
4 Three-dimensional side gather
4G First three-dimensional elastic member
4c First portion
4e First back fallen portion
4f First rising portion
4x Side root portion
5 Connecting tape
6 Target sheet
9 Connecting portion
20 Three-dimensional waist gather
21 Second three-dimensional elastic member
22 Waist root portion
23 Second portion
24 Second fallen portion
25 Second rising portion
26 Three-dimensional waist sheet
31 Third three-dimensional elastic member
33 Third portion
34 Third fallen portion
35 Third rising portion
B Dorsal side portion
EF End flap
F Ventral side portion
LD Front-back direction
SF Side flap
WD Width direction

The invention claimed is:

1. A connecting-type disposable wearing article comprising:
a crotch portion including a center in a front-back direction;
a ventral side portion extending from the center in the front-back direction to a front side;
a dorsal side portion extending from the center in the front-back direction to a back side;
connecting portions provided in both side portions of the dorsal side portion and configured to be detachably connected to an external surface of the ventral side portion;
three-dimensional side gathers rising from a front surface are provided along first blocking positions disposed in both sides in a width direction,
each of the three-dimensional side gathers having a side root portion attached to an outside in the width direction of the first blocking position, a first portion extending from the side root portion, a first front fallen portion and a first back fallen portion formed by fixing a front end portion and a back end portion of the first portion in a fallen state, respectively, a first rising portion formed to be non-fixed between the first front fallen portion and the first back fallen portion in the first portion, and a first three-dimensional elastic member attached at least to a tip portion of the first rising portion, and
at least the tip portion of the first rising portion being contracted in the front-back direction together with the first three-dimensional elastic member and extensible in the front-back direction; and
a three-dimensional waist gather rising from the front surface is provided along a second blocking position disposed at least one of between both the first front fallen portions and between both the first back fallen portions,
the three-dimensional waist gather having a waist root portion attached along the second blocking position, a second portion extending from the waist root portion toward a waist edge side, second fallen portions formed by fixing both end portions in the width direction of the second portion in a fallen state, respectively, a second rising portion formed to be non-fixed between the second fallen portions in the second portion, and a second three-dimensional elastic member attached at least to a tip portion of the second rising portion, at least the tip portion of the second rising portion being contracted in the width direction together with the second three-dimensional elastic member and extensible in the width direction, and the three-dimensional waist gather has:
- a third portion extending from the waist root portion toward a crotch side;
- third fallen portions formed by fixing both end portions in the width direction of the third portion in a fallen state, respectively;
- a third rising portion formed to be non-fixed between the third fallen portions in the third portion; and
- a third three-dimensional elastic member attached at least to a tip portion of the third rising portion.

2. The connecting-type disposable wearing article according to claim 1, wherein in a state where the wearing article is spread, the three-dimensional waist gather has the second three-dimensional elastic member located closer to a waist edge than the connecting portions.

3. The connecting-type disposable wearing article according to claim 2, wherein the second three-dimensional elastic member is a plurality of second three-dimensional elastic members provided at intervals in the front-back direction, and a stretch rate of each of the second three-dimensional elastic members in a state where the wearing article is spread decreases toward the waist edge side.

4. The connecting-type disposable wearing article according to claim 1, wherein the second three-dimensional elastic member is a plurality of second three-dimensional elastic members provided at intervals in the front-back direction, and a stretch rate of each of the second three-dimensional elastic members in a state where the wearing article is spread decreases toward the waist edge side.

5. The connecting-type disposable wearing article according to claim 1, wherein the second three-dimensional elastic member is a plurality of second three-dimensional elastic members provided at intervals in the front-back direction, and a stretch rate of each of the second three-dimensional elastic members in a state where the wearing article is spread decreases toward the waist edge side.

* * * * *